(12) United States Patent
Bledsoe et al.

(10) Patent No.: US 6,919,477 B2
(45) Date of Patent: Jul. 19, 2005

(54) FRUITY MUSK COMPOSITIONS

(75) Inventors: James O. Bledsoe, Neptune Beach, FL (US); Michael Britten-Kelly, Jacksonville, FL (US); Mark A. Sprecker, Sea Bright, NJ (US); Robert P. Belko, Monroe, NJ (US); Manfred Pawlak, Princeton, NJ (US); Michael G. Monteleone, Matawan, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 107 days.

(21) Appl. No.: 10/845,935

(22) Filed: May 14, 2004

(65) Prior Publication Data
US 2004/0214745 A1 Oct. 28, 2004

Related U.S. Application Data

(62) Division of application No. 10/243,143, filed on Sep. 14, 2002, now Pat. No. 6,774,260.

(51) Int. Cl.[7] .............................................. C07C 69/34
(52) U.S. Cl. ........................... 560/193; 560/190; 512/8; 512/26
(58) Field of Search ................................ 560/129, 190, 560/193; 512/8, 25, 26

(56) References Cited

U.S. PATENT DOCUMENTS

| 3,487,102 A | 12/1969 | Blumenthal |
| 4,534,891 A | 8/1985 | Boden et al. |
| 6,384,242 B1 | 5/2002 | Fankhauser et al. |
| 6,384,269 B1 | 5/2002 | Williams |

FOREIGN PATENT DOCUMENTS

| FR | 2008167 | 1/1970 |
| WO | WO 00/14051 | 3/2000 |

Primary Examiner—Johann Richter
Assistant Examiner—Karl Puttlitz
(74) Attorney, Agent, or Firm—Joseph F. Leightner

(57) ABSTRACT

Novel ester compounds and the use of these esters as a fragrance chemicals, suitable for use in creating fragrance, and scents in items such as perfumes, colognes and personal care products are disclosed.

6 Claims, No Drawings

FRUITY MUSK COMPOSITIONS

STATUS OF RELATED APPLICATIONS

This application is a divisional of U.S. Ser. No. 10/243,143, filed on Sep. 14, 2002 now U.S. Pat. No. 6,774,260, the contents hereby incorporated by reference as if set forth in its entirety.

FIELD OF THE INVENTION

This invention demonstrates that certain keto esters, carbonates, and diesters of alcohols, which comprise newly discovered chemicals, are useful as fragrance chemicals, which add value when used in fine fragrances, cosmetics, toiletries, and related applications.

BACKGROUND OF THE INVENTION

There is an ongoing need in the fragrance industry to provide new chemicals to give perfumers and other persons ability to create new fragrances for perfumes, colognes and personal care products.

The use of alcohols and esters in perfume materials is disclosed. See for example, U.S. Pat. Nos. 3,487,102, 6,384,242, and 6,384,269, which disclose alkonates, geranic acid derivatives and esters respectively, that are suitable as fragrance materials.

Despite these disclosures and availability of commercial products there is an ongoing need for the development of new fragrance chemicals that can be used to provide pleasant fragrance to various products.

SUMMARY OF THE INVENTION

The present invention is directed to the following novel compounds and use of these novel compounds as fragrance chemicals to enhance fragrance in perfumes, toilet waters, colognes, personal products and the like. More specifically, the present invention is a method for enhancing a perfume by incorporating an olfactory acceptable amount of compounds of the Formula I, II and III shown below:

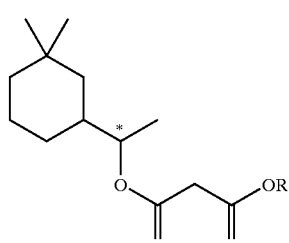

I

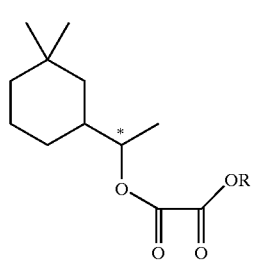

II

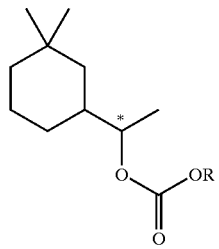

III where R is selected from methyl [CH3]; ethyl [C2H5] and isopropyl [C3H7].

As those with skill in the art will appreciate, the above structures contain chiral centers. The positions designated with a * may have the absolute configuration of "R", "S" or racemic. The present invention includes these racemic mixtures as well as the entantiomers described herein which are suitable as fragrance materials. These and other embodiments of the present invention will be apparent by reading the following specification.

DETAILED DESCRIPTION OF THE INVENTION

The present invention discloses the composition of new chemical entities, not previously disclosed. Furthermore, the present invention is directed to the use of the compounds, set forth above, in various fragrance applications.

We have discovered that these compounds have a fruity, musky odor or note, that is well suited for use as a fragrance chemical, and impart fresh, vibrant, and long-lasting characteristics to perfume and fragrance formulations.

Using formulae set forth above, the described compounds are the following:

| Formula | R | Compound |
|---|---|---|
| I | methyl | 1-(3,3-dimethylcyclohexyl) methyl malonate |
| I | ethyl | 1-(3,3-dimethylcyclohexyl) ethyl malonate |
| I | propyl | 1-(3,3-dimethylcyclohexyl) propyl malonate |
| I | isopropyl | 1-(3,3-dimethylcyclohexyl) isopropyl malonate |
| II | methyl | 1-(3,3-dimethylcyclohexyl) methyl oxalate |
| II | ethyl | 1-(3,3-dimethylcyclohexyl) ethyl oxalate |
| II | propyl | 1-(3,3-dimethylcyclohexyl) propyl oxalate |
| II | isopropryl | 1-(3,3-dimethylcyclohexyl) isopropyl oxalate |
| III | methyl | 1-(3,3-dimethylcyclohexyl) methyl carbonate |
| III | ethyl | 1-(3,3-dimethylcyclohexyl) ethyl carbonate |
| III | propyl | 1-(3,3-dimethylcyclohexyl) propyl carbonate |
| III | isopropyl | 1-(3,3-dimethylcyclohexyl) isopropyl carbonate |

The use of these compounds are widely applicable in current perfumery products, including the preparation of perfumes and colognes, the perfuming of personal care products such as soaps, shower gels, and hair care products, as well as air fresheners, candles and cosmetic products. The compounds can also be used to perfume cleaning agents, such as, but not limited to soaps, detergents, dishwashing materials, scrubbing compositions, window cleaners, and the like.

In these preparations, the compound of the present invention can be used alone or in combination with other fragrance compositions, solvents, adjuvants and the like. Those with skill in the art will appreciate the nature and variety of the other ingredients that can be used in combination with the compound of the present invention.

Many types of fragrances can be employed in the present invention, the only limitation being the compatibility with the other components being employed. Suitable fragrances include, but are not limited to fruit essences such as almond, apple, cherry, grape, pear, pineapple, orange, strawberry, raspberry; musk; and flower scents such as lavender, rose, iris, and carnation. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

As used herein olfactory effective amount is understood to mean the amount of compound in perfume compositions the individual component will contribute to its particular olfactory characteristics, but the olfactory effect of the perfume composition will be the sum of the effects of each of the perfume or fragrance ingredients. Thus the compounds of the invention can be used to alter the aroma characteristics of the perfume composition by modifying the olfactory reaction contributed by another ingredient in the composition. The amount will vary depending on many factors including other ingredients, their relative amounts and the effect that is desired.

The level of compound of the invention employed in the perfumed article varies from about 0.05 to about 40 weight percent, preferably from about 0.1 to about 10 and most preferably from about 1 to about 5 weight percent. In addition to the compounds, other agents can be used in conjunction with the fragrance. Well known materials such as surfactants, emulsifiers, and polymers to encapsulate the fragrance can also be employed without departing from the scope of the present invention.

Another method of reporting the level of the compound of the invention in the perfumed composition, i.e., the compounds as a weight percentage of the materials added to impart the desired fragrance. The compounds of the invention can range widely from 0.005 to about 10 weight percent of the perfumed composition, and preferably from about 0.1 to about 5 weight percent. Those with skill in the art will be able to employ the desired level of the compound of the invention to provide the desired fragrance and intensity.

The compounds are prepared by standard traditional esterification methods. The starting materials for these compounds is the readily available alcohol alpha,3,3-trimethylcyclohexylmethanol, as disclosed in U.S. Pat. No. 3,487,102, the contents of which are incorporated by reference. This alcohol is then reacted with the corresponding malonate, oxalate or carbonate esters to provide the compounds of the invention, using standard esterification catalysts and reagents.

The various enantiomers of the invention may be provided by methods known in the art. One method for producing the enantiomers is stereoselective enzymatic hydrolysis of the racemic ester groups. As those with skill in the art appreciate, an enzyme is selected which selectively hydrolyzed only one enantiomeric ester to the corresponding alcohol, one enantiomer, thereby providing only the other antipodal ester.

Another and preferred method for providing a desired enantiomer of the invention is to employ a chiral alcohol as a starting material and the corresponding acid to form a series of entantiomerically pure esters.

The following are provided as specific embodiments of the present invention. Other modifications of this invention will be readily apparent to those skilled in the art, without departing from the scope of this invention. As used herein, all percentages are weight percent. IFF as used in the examples is understood to mean International Flavors & Fragrances Inc., DPG is understood to mean dipropylene glycol, DEP is understood to mean diethyl phthalate. All of the fragrance chemicals used in the examples can be purchased from IFF, N.Y., N.Y., unless otherwise noted.

EXAMPLE 1

Preparation of Ethyl 1-(3,3-dimethylcyclohexyl) Ethyl Malonate

A solution of 2000 grams of diethyl malonate and 500 grams of alpha, 3,3-trimethylcyclohexanemethanol was heated to 160° C., while distilling off ethanol. Vacuum distillation provided 809 grams of product.

The product had a fruity odor, with apple, pear and musky notes predominating. The odor was long-lasting, survivng 3 days on a smelling blotter.

The boiling point of the product was 138° C. at 3.5 millimeters of mercury.

The NMR analysis of the product is the following:
0.81–1.66 ppm (m, 9H);0.88 ppm (s, 3H);0.91 ppm (s, 3H);1.19 ppm (d, 3H, J=6.4Hz);1.29 ppm (t, 3H, J=7.1 Hz);3.35 ppm (s, 4H);4.21 ppm (q, 2H);4.75 ppm (m, 1H).

EXAMPLE 2

Preparation of Methyl 1-(3,3-dimethylcyclohexyl) Methyl Oxalate

A solution of 2000 grams of dimethyl oxalate and 500 grams of alpha, 3,3-trimethylcyclohexanemethanol was heated to 165° C., while distilling off methanol. Vacuum distillation provided 633 grams of product. The product had a boiling point of 141° C. at 65 millimeters of mercury.

The product had a weak musk note, lasting 24 hours on a smelling blotter.

The NMR analysis of the product is the following.
0.82–1.88 ppm (m, 9H);0.87 ppm (s, 3H);0.90 ppm (s, 3H);1.26 ppm (d, 3H, J=6.4 Hz);
3.88 ppm (s, 4H);4.85 ppm (m, 1H).

EXAMPLE 3

Preparation of Ethyl 1-(3,3-dimethylcyclohexyl) Methyl Oxalate 50.2 grams (0.36 moles) of ethyl chlorooxalate was added dropwise to a stirred solution of 46.8 grams (0.3 moles) of alpha-3,3-trimethylcyclohexanemethanol and 35.6 grams (0.45 moles) of pyridine at 25–30° C. The solution was stirred for one hour at ambient temperature. The reaction mixture was diluted with 100 milliliters of heptane, extracted with 100 milliliters of 5 weight percent HCl, and washed successively with water and 15 weight percent sodium carbonate. Distillation provided 57.3 grams of product.

The boiling point of product was 98° C. at 0.5 millimeters of mercury. The product had a musky, woody note, lasting 10 hours on a smelling blotter.

The NMR analysis of the product was the following: 0.71–2.14 ppm(m, 9H);0.88 ppm (s, 3H);0.92 ppm (s, 3H);1.28 ppm (d, 3H, J=6.4 Hz); 1.38 ppm (t, 3H, J=6.3 Hz);4.34 ppm (m, 2H,);4.86 ppm (m, 1H).

EXAMPLE 4

Preparation of Isopropyl 1-(3,3-dimethylcyclohexyl) Isopropyl Malonate

A solution of 500 grams of alpha,3,3-trimethylcyclohexanemethanol and 100 grams of diisopropylmalonate was heated to 165° C. Vacuum distillation provided 474 grams of product. The product had a boiling point of 140° C. at 3.5 mm of mercury. The product had a weak musk note.

The NMR analysis of the product was the following: 0.81–1.68 ppm (m, 9H);0.88 ppm (s, 3H);1.19 ppm (d, 3H, J=6.4 Hz);1.27 ppm (d, 6H, J=6.3 Hz);3.32 ppm (s, 2H,);4.75 ppm (m, 1H);5.06 ppm (septtet, 1H, J=6.2 Hz).

EXAMPLE 5

Preparation of Ethyl 1-(3,3-dimethylcyclohexyl) Ethyl Carbonate

A solution of 500 grams of alpha,3,3-trimethylcyclohexanemethanol, 100 grams of 20 weight percent sodium ethylate solution and 590 grams of diethylcarbonate was heated at reflux for 12 hours. The reaction mass was cooled and diluted with 1 liter of 5 weight percent formic acid. The layers were split. Excess diethyl carbonate was removed under reduced pressure. Vacuum distillation provided 180 grams of product having a boiling point of 107° C. at 5 millimeters of mercury. The product had a bright fruity berry note, with woody, rose undertones.

The NMR analysis of the product was the following. 0.82–1.85 ppm (m, 9H);0.88 ppm (s, 3H);0.91 ppm (s, 3H);1.23 ppm (d, 3H, J=6.4 Hz);1.31 ppm (t, 3H, J=7.1 Hz);4.18 ppm (q, 2H, J=7.1 Hz);4.54 ppm (pentet, 1H, J=6.2 Hz).

EXAMPLE 6

Use of the Fragrance Compounds Prepared in a Fragrance Composition

The fragrance compounds prepared in Examples 1, 3 and 4 above, were used together in the following formulation to provide a fragrance with citrus notes.

| Ingredients | Parts by Weight |
| --- | --- |
| Material from Example 4 | 50.00 |
| Ethyl Vanillin 10% DPG | 5.00 |
| Material from Example 1 | 40.00 |
| Material from Example 3 | 128.00 |
| HEDIONE (Firmenich) | 10.00 |
| Vanillin 10% PG | 10.00 |
| Ambrette Seed Oil | 0.30 |
| Bergamot Oil | 40.00 |
| Patchouli Oil Light 10% DPG | 5.00 |
| Dipropylene Glycol | 131.70 |

EXAMPLE 7

Fragrance Formulations

Three different citrus fragrances were prepared using the fragrance compounds prepared in Examples 1, 2 and 3 described above.

| Ingredients | Version E Parts by Weight | Version F Parts by Weight | Version G Parts by Weight |
| --- | --- | --- | --- |
| Ethyl Vanillin 10% DPG | 5.00 | 5.00 | 5.00 |
| Material from Example 1 | — | — | 218.00 |
| HEDIONE (Firmenich) | 10.00 | 10.00 | 10.00 |
| Vanillin 10% PG | 10.00 | 10.00 | 10.00 |
| Ambrette Seed Oil | 0.30 | 0.30 | 0.30 |
| Bergamot Oil | 40.00 | 40.00 | 40.00 |
| Patchouli Oil Light 10% DPG | 5.00 | 5.00 | 5.00 |
| Dipropylene Glycol | 131.70 | 131.70 | 131.70 |
| Material from Example 2 | — | 218.00 | — |
| Material from Example 3 | 218.00 | — | — |

The mixtures were found to provide pleasant fragrances with citrus notes.

EXAMPLE 8

Fragrance Formulations

Three different citrus/musk versions were prepared using the fragrance materials prepared in Examples 3, 4 and 5 described above.

| Ingredients | Version E Parts by Weight | Version F Parts by Weight | Version G Parts by Weight |
| --- | --- | --- | --- |
| Material from Example 3 | 218.00 | — | — |
| Ethyl Vanillin 10% DPG | 5.00 | 5.00 | 5.00 |
| Material from Example 4 | — | 218.00 | — |
| Material from Example 5 | — | — | 218.00 |
| HEDIONE (Firmenich) | 10.00 | 10.00 | 10.00 |
| Vanillin 10% PG | 10.00 | 10.00 | 10.00 |
| Ambrette Seed Oil | 0.30 | 0.30 | 0.30 |
| Bergamot Oil | 40.00 | 40.00 | 40.00 |
| Patchouli Oil Light 10% DPG | 5.00 | 5.00 | 5.00 |
| Dipropylene Glycol | 131.70 | 131.70 | 131.70 |

The above fragrances were found to provide pleasing acceptable fragrances with musky notes and citrus characteristics.

EXAMPLE 9

Use of the Compound of the Present Invention

Two fragrance formulations were prepared with similar formulations, except that a compound of the present invention is employed and a homolog compound is employed in the second formulation. The oriental-type fragrance, the formulations are set forth below:

| Ingredients | Formulation H Parts by Weight | Formulation I Parts by Weight |
|---|---|---|
| Ethyl Vanillin 10% DPG | 5.00 | 5.00 |
| Material from Example 1 Fret 02-050 | 218.00 | None |
| Butanedioc acid, 1-(3,3-dimethylcyclohexyl)-ethyl ethyl ester Strawberry Musk compound (Firmenich) IFF fret 02-0138 | None | 218.00 |
| KHARISMAL | 10.00 | 10.00 |
| Vanillin ex Lignin 10% DPG | 10.00 | 10.00 |
| Ambrette Seed Oil | 0.30 | 0.30 |
| Bergamot Essential Oil | 40.00 | 40.00 |
| Patchouli Oil 10% DPG | 5.00 | 5.00 |
| DPG | 131.70 | 131.70 |
| AMBERIFF crystals 1% DPG | 10.00 | 10.00 |

The use of the compound from Example 1 Formulation H creates an aura of sensual musk with softer overtones of amber and citrus. The use of the homolog material in Formulation I provides a fragrance that has a weak musk character, with a more citrus character and undertones of sweet fruit. This example demonstrates that the compounds of the present invention are surprisingly a more powerful musk fragrance chemical, having less citrus and sweet fruit notes than structurally similar fragrance materials.

What is claimed is:

1. A method for improving, enhancing or modifying a fragrance through the addition of an olfactory acceptable amount of the compounds selected from the group consisting of:

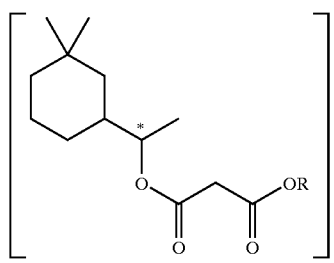

I

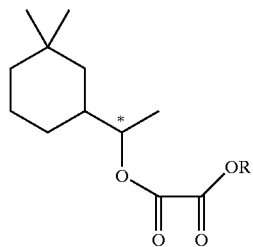

II

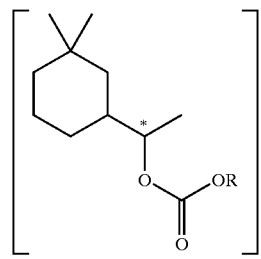

III where R is selected from methyl, ethyl or isopropyl and the carbon atom designated with an asterisk * has the absolute configuration of "R" or "S".

2. The method of claim 1 wherein the fragrance is incorporated into a product selected from the group consisting of perfumes, colognes, candles, toilet waters, cosmetic products, personal care products, fabric care products, cleaning products and air fresheners.

3. The method of claim 2 wherein the cleaning product is selected from the group consisting of soaps, detergents, dishwashing compositions, scrubbing compounds and window cleaners.

4. The method of claim 2 wherein the product is a personal care product.

5. The method of claim 1 wherein said olfactory acceptable amount is from about 0.05 to about 40 weight percent.

6. The method of claim 1 wherein said olfactory acceptable amount is from about 0.1 to about 10 weight percent.

* * * * *